United States Patent
Speyer (10) Patent No.: US 10,286,080 B2
(45) Date of Patent: May 14, 2019

(54) IGA FC-FOLATE CONJUGATES, PHARMACEUTICAL COMPOSITIONS AND METHODS TO TREAT CANCER

(71) Applicant: Cecilia Speyer, Novi, MI (US)

(72) Inventor: Cecilia Speyer, Novi, MI (US)

(73) Assignee: Wayne State University, Detroit, MI (US)

( * ) Notice: Subject to any disclaimer, the term of this patent is extended or adjusted under 35 U.S.C. 154(b) by 27 days.

(21) Appl. No.: 15/227,747

(22) Filed: Aug. 3, 2016

(65) Prior Publication Data
US 2017/0035901 A1 Feb. 9, 2017

Related U.S. Application Data

(60) Provisional application No. 62/200,463, filed on Aug. 3, 2015.

(51) Int. Cl.
*A61K 47/68* (2017.01)
*A61K 47/55* (2017.01)

(52) U.S. Cl.
CPC ............ *A61K 47/68* (2017.08); *A61K 47/551* (2017.08)

(58) Field of Classification Search
None
See application file for complete search history.

(56) References Cited

U.S. PATENT DOCUMENTS

| | | | |
|---|---|---|---|
| 5,500,362 A | 3/1996 | Robinson et al. | |
| 5,821,337 A | 10/1998 | Carter et al. | |
| 6,291,673 B1* | 9/2001 | Fuchs ................. | C07D 475/04 544/258 |
| 2004/0242582 A1 | 12/2004 | Green et al. | |
| 2005/0227985 A9 | 10/2005 | Green et al. | |
| 2006/0024298 A1* | 2/2006 | Lazar ................. | C07K 16/2893 424/133.1 |
| 2013/0259882 A1* | 10/2013 | Liu ................. | A61K 47/48384 424/181.1 |

OTHER PUBLICATIONS

Otten et al. (J Immunol, 174: 5472-5480, 2005).*
Townsend et al. (Biomedicine and Pharmacotherapy, 57: 145-155, 2003).*
Zhang et al. (Arch Pathol Lab Med, 138: 890-895, Jul. 2014).*
Abdallah, et al., "Mouse neutrophils are professional antigen-presenting cells programmed to instruct Th1 and Th17 T-cell differentiation", Int. Immunol., vol. 23, No. 5, 2011, pp. 317-326.
Bakema, et al., "Immunoglobulin A: A next generation of therapeutic antibodies?", mAbs, vol. 3, No. 4, 2011, pp. 352-361.
Bakema, et al., "Targeting FcalphaRI on polymorphonuclear cells induces tumor cell killing through autophagy," J Immunol., vol. 187, 2011, pp. 726-732.
BreastCancer.org: How triple-negative breast cancer behaves and looks., 2013 (http://www.breastcancer.org/symptoms/diagnosis/trip_neg/behavior), 2 pages.
Cho, et al., "Single-chain Fv/folate conjugates mediate efficient lysis of folate-receptor-positive tumor cells," Bioconjugate Chem., vol. 8, 1997, pp. 338-346.
Cleere, "Triple-negative breast cancer: a clinical update," Community Oncology, vol. 7, 2010, pp. 203-211.
Clynes, et al., "Inhibitory Fc receptors modulate in vivo cytotoxicity against tumor targets," Nature Medicine, vol. 6, 2000, pp. 443-446.
Czajkowsky, et al., "Fc-fusion proteins: new developments and future perspectives," EMBO Mol. Med., vol. 4, 2012, pp. 1015-1028.
Deo, et al., "Bispecific molecules directed to the Fc receptor for IgA (Fc alpha RI, CD89) and tumor antigens efficiently promote cell-mediated cytotoxicity of tumor targets in whole blood," J. Immunol., vol. 160, 1998, pp. 1677-1686.
Ebel et al., "Preclinical evaluation of MORAb-003, a humanized monoclonal antibody antagonizing folate receptor-alpha," Cancer Immunity, vol. 6, 2007, 8 pages.
Elnakat, et al., "Distribution, functionality and gene regulation of folate receptor isoforms: implications in targeted therapy," Adv. Drug Deliv. Rev., vol. 56, 2004, pp. 1067-1084.
Ethier, et al., "Differential isolation of normal luminal mammary epithelial cells and breast cancer cells from primary and metastatic sites using selective media," Cancer Res., vol. 53, 1993, pp. 627-635.
Feuerstein A: Endocyte Falls on Ovarian Cancer Drug Blowup, The Street May 2014, https://www.thestreet.com/story/12693261/1/endocyte-falls-on-ovarian-cancer-drug-blowup.html, 4 pages.
Fridlender, et al., "Transcriptomic analysis comparing tumor-associated neutrophils with granulocytic myeloid-derived suppressor cells and normal neutrophils," PLoS One, vol. 7, No. 2, 2012, 13 pages.
Guettinger, et al., "A recombinant bispecific single-chain fragment variable specific for HLA class II and Fc alpha RI (CD89) recruits polymorphonuclear neutrophils for efficient lysis of malignant B lymphoid cells," J. Immunol., vol. 184, 2010, pp. 1210-1217.
Hamre, et al., "Expression and modulation of the human immunoglobulin A Fc receptor (CD89) and the FcR gamma chain on myeloid cells in blood and tissue," Scandinavian J. Immuno., vol. 57, 2003, pp. 506-516.
Huls, et al., "Antitumor immune effector mechanisms recruited by phage display-derived fully human IgG1 and IgA1 monoclonal antibodies," Cancer Research, vol. 59, 1999, pp. 5778-5784.
Iking-Konert, et al., "Polymorphonuclear neutrophils in Wegener's granulomatosis acquire characteristics of antigen presenting cells," Kidney Int., vol. 60, 2001, pp. 2247-2262.
Kane, et al., "Influence on immunoreactive folate-binding proteins of extracellular folate concentration in cultured human cells," J. Clin. Invest., vol. 81, 1988, pp. 1398-1406.

(Continued)

*Primary Examiner* — Nelson B Moseley, II
(74) *Attorney, Agent, or Firm* — Lee & Hayes, P.C.; C. Rachal Winger; Tanya Harding (57) ABSTRACT

IgA-based Fc-folate conjugates as a treatment for cancer are provided. The conjugates utilize only the Fc portion of IgA to target its receptor on neutrophils (FcαR1) to elicit antibody-dependent cellular-cytotoxicity (ADCC).

19 Claims, 4 Drawing Sheets

(56) References Cited

OTHER PUBLICATIONS

Li, et al., "Folate-immunoglobulin G as an anticancer therapeutic antibody," Bioconjugate Chem., vol. 21, 2010, pp. 961-968.
Lohse, et al., "Recombinant dimeric IgA antibodies against the epidermal growth factor receptor mediate effective tumor cell killing," J. Immunol., vol. 186, 2011, pp. 3770-3778.
Low, et al., "Folate-targeted therapeutic and imaging agents for cancer," Curr. Opin. Chem. Biol., vol. 13, 2009, pp. 256-262.
Monteiro, et al., "IgA Fc receptors," Annu. Rev. Immunol., vol. 21, 2003, pp. 177-204.
Morton, et al., "Structure and function of human IgA Fc receptors (Fc alpha R)," Critical Reviews in Immunology, vol. 16, 1996, pp. 423-440.
O'Shannessy, et al, "Characterization of the human folate receptor alpha via novel antibody-based probes," Oncotarget, vol. 2, No. 12, 2011, pp. 1227-1243.
Parker, et al., "Folate receptor expression in carcinomas and normal tissues determined by a quantitative radioligand binding assay," Anal. Biochem., vol. 338, 2005, pp. 284-293.
Pohlmann, et al., "Resistance to Trastuzumab in Breast Cancer," Clinical cancer research : an official journal of the American Association for Cancer Research, vol. 15, No. 24, 2009, pp. 7479-7491.
Prabaharan, et al., "Folate-conjugated amphiphilic hyperbranched block copolymers based on Boltorn H40, poly(L-lactide) and poly-(ethylene glycol) for tumor-targeted drug delivery," Biomaterials, vol. 30, 2009, pp. 3009-3019.
Prabaharan, et al., "Thermosensitive micelles based on folate-conjugated poly(N-vinylcaprolactam)-block-poly (ethylene glycol) for tumor-targeted drug delivery," Macromol. Biosci., vol. 9, 2009, pp. 744-753.
Ravetch, et al., "IgG Fc receptors," Annu. Rev. Immunol., vol. 19, 2001, pp. 275-290.
Reljic, "In search of the elusive mouse macrophage Fc-alpha receptor," Immunol. Lett., vol. 107, 2006, pp. 80-81.
Repp, et al., "Phase I clinical trial of the bispecific antibody MDX-H210 (anti-FcgammaRI x anti-HER-2/neu) in combination with Filgrastim (G-CSF) for treatment of advanced breast cancer," British J. Cancer, vol. 89, 2003, pp. 2234-2243.
Rudnick, et al. "Influence of affinity and antigen internalization on the uptake and penetration of Anti-HER2 antibodies in solid tumors," Cancer Res., vol. 71, No. 6, 2011, pp. 2250-2259.
Siegel R., Cancer Statistics 2014, Cancer Journal for Clinicians 2014, vol. 64, 2014, pp. 9-29; Published online ahead of print at cacancerjournal.com. doi: 10.3322/caac.21208.
Speyer, et al., "Metabotropic glutamate receptor-1: a potential therapeutic target for the treatment of breast cancer," Breast Cancer Res. Treat., vol. 132, 2012, pp. 565-573.
Speyer, et al., "Novel chemokine responsiveness and mobilization of neutrophils during sepsis," Am. J. Pathol., vol. 165, No. 6, 2004, pp. 2187-2196.
Stewart, et al., "Unaggregated serum IgA binds to neutrophil Fc alpha R at physiological concentrations and is endocytosed but cross-linking is necessary to elicit a respiratory burst," J. Leukoc. Biol., vol. 56, 1994, pp. 481-487.
Stockmeyer, et al., "Mechanisms of G-CSF- or GM-CSF-stimulated tumor cell killing by Fc receptor-directed bispecific antibodies," J. Immuno. Meth., vol. 248, 2001, pp. 103-111.
Stover, "Physiology of folate and vitamin B12 in health and disease," Nutrition Reviews, vol. 62, 2004, pp. S3-S12; discussion S13.
Taylor, Breast Cancer Drug Market 'Set to be Static' to 2019: The breast cancer drug market will remain largely static over the next decade, owing to the generic erosion of key agents and a substantial reduction in the prescribing of Roche/Genentech/Chugai's Avastin. Decision Resources, 2011, http://www.pharmatimes.com/news/breast_cancer_drug_market_set_to_be_static_to_2019_979266 (3 pages).
Tran, et al., "Enhancement of folate receptor alpha expression in tumor cells through the glucocorticoid receptor: a promising means to improved tumor detection and targeting", Cancer Res., vol. 65, No. 10, 2005, pp. 4431-4441.
Valerius, et al., "HLA class II antibodies recruit G-CSF activated neutrophils for treatment of B cell malignancies," Leukemia & Lymphoma, vol. 26, 1997, pp. 261-269.
Van Egmond, "Neutrophils in antibody-based immunotherapy of cancer," Expert Opin. Biol. Ther., vol. 8, 2008, pp. 83-94.
Van Egmond, et al., "Enhancement of polymorphonuclear cell-mediated tumor cell killing on simultaneous engagement of fcgammaRI (CD64) and fcalphaRI (CD89)," Cancer Res., vol. 61, 2001, pp. 4055-4060.
Van Egmond, et al., "Human immunoglobulin A receptor (FcalphaRI, CD89) function in transgenic mice requires both FcR gamma chain and CR3 (CD11b/CD18)", Blood, vol. 93, No. 12, 1999, pp. 4387-4394.
Van Egmond, et al., "IgA and the IgA Fc receptor," Trends in Immunol., vol. 22, 2001, pp. 205-211.
Weisbart, et al., "GM-CSF induces human neutrophil IgA-mediated phagocytosis by an IgA Fc receptor activation mechanism", Nature, vol. 332, 1988, pp. 647-648.
Weitman, et al., "Cellular localization of the folate receptor: potential role in drug toxicity and folate homeostasis," Cancer research, vol. 52, 1992, pp. 6708-6711.
Weitman, et al., "Distribution of the folate receptor GP38 in normal and malignant cell lines and tissues," Cancer Res., vol. 52, 1992, pp. 3396-3401.

* cited by examiner

FIG. 4

IGA FC-FOLATE CONJUGATES, PHARMACEUTICAL COMPOSITIONS AND METHODS TO TREAT CANCER

CROSS REFERENCE TO RELATED APPLICATION

This application claims priority to U.S. Provisional Patent Application No. 62/200,463 filed on Aug. 3, 2015, which is incorporated herein by reference in its entirety as if fully set forth herein.

FIELD OF THE DISCLOSURE

The present disclosure provides IgA antibody fragment crystallizable region (Fc)-Folate conjugates that selectively target and kill cancer cells expressing folate receptors. The Fc-Folate conjugates are particularly useful to treat breast cancer, including triple negative breast cancer, as well as ovarian and lung cancers.

BACKGROUND OF THE DISCLOSURE

According to the American Cancer Society, approximately 1 in 8 women in the U.S. will develop breast cancer at some point in their life (1). Of these women, 15-20% will be diagnosed with triple negative breast cancer (TNBC), an aggressive subtype of breast cancer with a high mortality rate (2). TNBC refers to breast tumors that lack the receptors for estrogen (ER), progesterone (PR), and epithelial growth factor (HER2) and therefore, are not dependent on them for growth. Because of this, these tumors do not respond to current hormonal therapy or therapy that targets the HER2 receptor. Of these women who are diagnosed with TNBC, approximately 23% will not survive five years (3). Of the women who survive beyond the first five years, another 20% will suffer a recurrence within 10 years of their treatment. Thus, although TNBC accounts for only 15-20% of new breast cancer patients, it is responsible for 66% of all breast cancer-related deaths (2).

SUMMARY OF THE DISCLOSURE

The high mortality rate of triple negative breast cancer (TNBC) is due to the fact that there is no effective targeted therapeutic treatment for TNBC. The only current treatment options involve the use of chemotherapeutic drugs that cause various toxicities by simply targeting highly replicating cells such as those of the immune system, the gastrointestinal epithelia and hair follicles. Thus, being able to directly target TNBC tumors would be beneficial in reducing mortality as well as reducing drug toxicity associated with these chemotherapeutic agents.

The present disclosure provides targeted therapies for TNBC in the form of IgA antibody Fc-folate conjugates.

BRIEF DESCRIPTION OF THE FIGURES

FIG. 4. PMN-mediated ADCC of TNBC cells in the presence of a folate-IgA conjugate. MDA-MB-468, or HeLa (control) cells were incubated with PMNs at a ratio of 1:10 (TNBC:PMN) in the presence of folate-IgA (5 µg/ml) or IgA (5 µg/ml) alone for 3 hours. After 3 hours, MTT substrate was added for 45 min. Results represent the absorbance values of the substrate which is indicative of cell viability. Cell viability was significantly reduced after treatment with folate-IgA in both the MDA-MB-468 and HeLa+PMN co-cultures compared to only IgA containing co-cultures. *P<0.05.

DETAILED DESCRIPTION

According to the American Cancer Society, approximately 1 in 8 women in the U.S. will develop breast cancer at some point in their life (1). Of these women, 15-20% will be diagnosed with triple negative breast cancer (TNBC), an aggressive subtype of breast cancer with a high mortality rate (2). TNBC refers to breast tumors that lack the receptors for estrogen (ER), progesterone (PR), and epithelial growth factor (HER2) and therefore, are not dependent on them for growth. Because of this, these tumors do not respond to current hormonal therapy such as tamoxifen or aromatase inhibitors or therapy that targets the HER2 receptor such as Herceptin (trastuzumab). Of these women who are diagnosed with TNBC, approximately 23% will not survive five years (3). Of the women who survive beyond the first five years, another 20% will suffer a recurrence within 10 years of their treatment. Thus, although TNBC accounts for only 15-20% of new breast cancer patients, it is responsible for 66% of all breast cancer-related deaths (2). This high mortality rate is due to the fact that there is no effective targeted therapeutic treatment for TNBC.

Folate is a small hydrophilic vitamin B molecule that is required for the synthesis of purines and pyrimidines, building blocks for DNA and RNA (42). Folate receptors constitute a family of proteins that together allow for the accumulation of folate in cells and may play a role in supporting growth in the developing embryo and fetus (43). In normal adult tissue, folate receptor alpha (FRA) shows limited expression with its expression being localized to apical surfaces of epithelial cells lining ducts within the kidneys, lungs, thyroid, breast and parotid glands (4, 5, 44, 45). Therefore, FRA in normal adult tissues is inaccessible through the bloodstream and hence normal tissues are spared from side effects of drugs that target FRA.

While in normal tissues FRA is not accessible via the vasculature, several malignant tumors over-express FRA, including those of the ovaries, lungs, colorectal, renal, and, recently, breast carcinomas (5, 6, 44, 45). In these tissues, FRA is accessible through the bloodstream. Thus, the restricted expression of FRA on the apical surface of normal tissue and its overexpression on malignant cells, makes it an attractive therapeutic target for cancer treatment.

Moreover, two studies recently found FRA expression to be strongly associated with ER/PR-negative and TNBC (>80%) status as well as poor prognosis with FRA expression associated with metastatic breast cancer and worse overall and disease-free survival (6,7). Taken together, these findings make FRA an attractive target for treating TNBC particularly.

The current disclosure includes use of folate itself (folic acid) as well as folate analogs that are also capable of binding to folate receptors.

Illustrative embodiments of folate analogs include folinic acid, pteropolyglutamic acid, and folate receptor-binding pteridines such as tetrahydropterins, dihydrofolates, tetrahydrofolates, and their deaza and dideaza analogs. The terms "deaza" and "dideaza" analogs refer to the art-recognized analogs having a carbon atom substituted for one or two nitrogen atoms in the naturally occurring folic acid structure, or analogs or derivatives thereof. For example, the deaza analogs include the 1-deaza, 3-deaza, 5-deaza, 8-deaza, and 10-deaza analogs of folate. The dideaza analogs include, for example, 1,5-dideaza, 5,10-dideaza, 8,10-dideaza, and 5,8-dideaza analogs of folate. Other folate analogs useful as complex forming ligands include the folate receptor-binding analogs am inopterin, amethopterin (methotrexate), $N^{10}$-methylfolate, 2-deamino-hydroxyfolate, deaza analogs such as 1-deazamethopterin or 3-deazamethopterin, and 3',5'-dichloro-4-amino-4-deoxy-$N^{10}$-methylpteroylglutamic acid (dichloromethotrexate). The foregoing folic acid analogs are conventionally termed folates, reflecting their ability to bind with folate-receptors. Additional analogs of folic acid that bind to folic acid receptors are described in U.S. Patent Application Publication Serial Nos. 2005/0227985 and 2004/0242582.

The basic antibody structural unit includes a tetramer. Each tetramer is composed of two pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region (the fragment crystallizable or "Fc" region) primarily responsible for effector function. Depending on the amino acid sequence of the heavy chain constant region, a given human antibody or immunoglobulin can be assigned to one of five major classes of immunoglobulins: IgA, IgD, IgE, IgG, and IgM. Several of these classes may be further divided into subclasses (isotypes), e.g., IgG1 (gamma 1), IgG2 (gamma 2), IgG3 (gamma 3), and IgG4 (gamma 4), and IgA1 and IgA2. The structures and three-dimensional configurations of different classes of immunoglobulins are well-known and relevant sequences are available in publicly-accessible databases, such as PubMed. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)).

"Antibody-dependent cell-mediated cytotoxicity" (ADCC) refers to a cell-mediated reaction in which non-specific cytotoxic cells that express Ig Fc receptors (FcRs) (e.g. Natural Killer (NK) cells, monocytes, neutrophils, and macrophages) recognize bound antibody (or a fragment thereof) on a target cell and subsequently cause lysis of the target cell (e.g., a cancer cell). FcR expression on hematopoietic cells is summarized in Table 3 on page 464 of Ravetch and Kinet, Annu. Rev. Immunol 9:457-92 (1991). To assess ADCC activity of a conjugate disclosed herein in vitro ADCC assays, such as those described herein and/or in U.S. Pat. No. 5,500,362, or 5,821,337 can be performed. Useful effector cells for such assays include peripheral blood mononuclear cells (PBMC).

Monoclonal antibodies currently in use in the clinic for the treatment of a number of diseases, including several malignancies, are of the IgG isoform. These antibodies were engineered with the sole intent to inhibit a major signaling pathway critical for the progression of disease, such as Herceptin to inhibit cell growth, in the treatment of HER2+ breast cancer. Later, it was discovered that some of these antibodies, in addition to their primary function, were also capable of stimulating ADCC through the binding of their Fc portion to their respective FcγIII receptors on macrophages, PMNs and NK cells (21,22). This finding led to the modification of some of these antibodies and the development of combined therapies using FcγIII-activating immunocytokines (G-CSF) in conjunction with bispecific antibodies targeting both cancer cells and FcγIII to increase their ADCC potential (23,25). However, the ADCC response mediated through FcγIII is weak possibility due to their low expression level, the presence of high levels of competing IgG antibodies in serum, their presence on other non-cytotoxic cells and the presence of inhibitory FcγIII receptors (21, 26) and thus, requires administration of various immunocytokines such as G-CSF to increase their effectiveness.

FcαR1, on the other hand, is expressed only on cytotoxic cells and in high numbers on PMNs making this receptor a very potent mediator of ADCC independent of any immunocytokine co-factors(27). The concept of targeting FcαR1 using monoclonal or bispecific IgA antibodies targeting this receptor to elicit cancer cell killing by PMNs has been tested successfully in vitro (10, 11, 28-33) where IgA also showed superiority over IgG. However, research into the potential therapeutic use of FcαR1 is hampered by the lack of adequate mouse models because mice do not express FcαR1 and the lack of established models for production and purification of high levels of IgA (34).

The current disclosure demonstrates the binding of novel FRA-binding conjugates to FRA-expressing cancer cells, such as TNBC cells. Upon binding, the conjugate is able to recruit and activate neutrophils (PMNs), the major white blood cell in humans, to destroy the cancer cell. These findings suggest the use of a conjugate of this type could effectively kill cancer cells and thus represents a promising effective targeted therapeutic treatment for cancer, such as TNBC.

Figure 1:
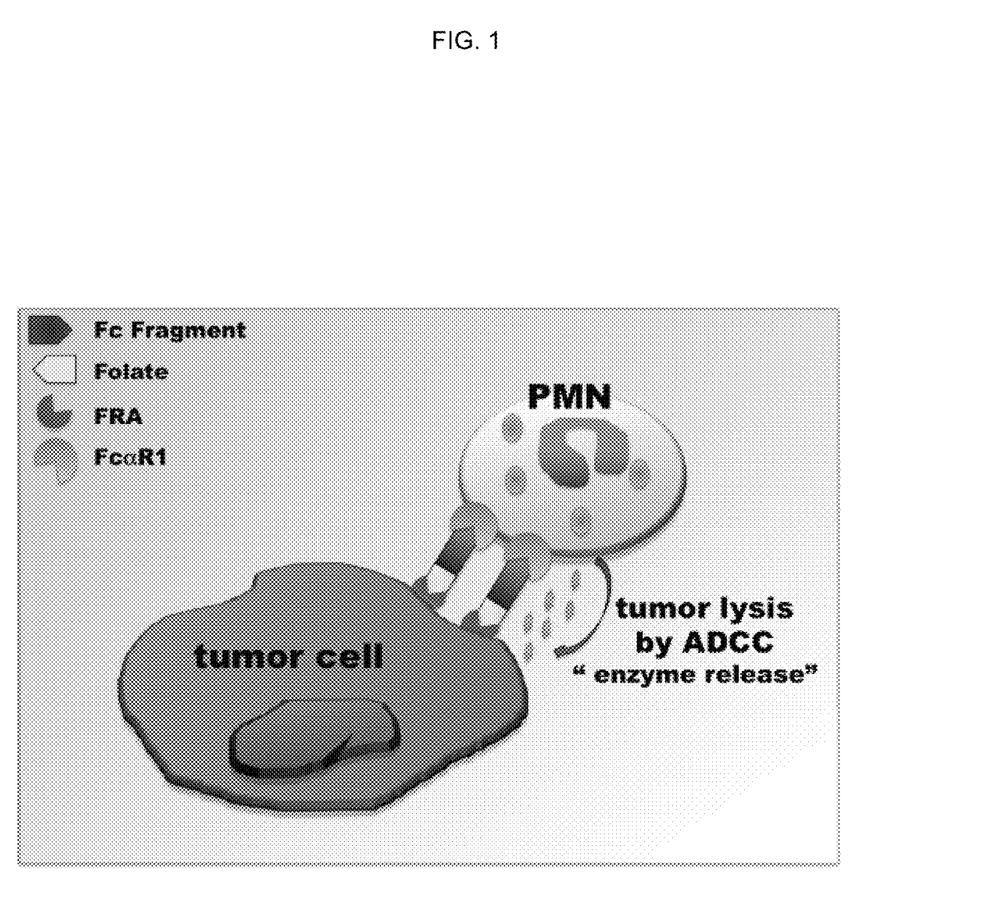
FIG. 1. An Fc-folate conjugate triggers neutrophil (PMN)-mediated cancer cell apoptosis by antibody-dependent cellular-cytotoxicity (ADCC). Binding of the folate component of the conjugate to its folate receptor (FRA) present on cancer cells allows binding of the Fc fragment to its receptor (FcαRI) on the PMN. This binding cross-links FcαRI receptors, triggering ADCC through the release of cytotoxic enzymes resulting in cancer cell apoptosis.

Accordingly, the present disclosure provides novel FRA-binding conjugates (in one embodiment, referred to as "NEU1") that elicit the immune system to target and kill TNBC cells. This approach takes advantage of the recent identification of folate receptor type alpha (FRA) on TNBC tissue as well as the numerous studies documenting PMNs as potent effector cells for IgA-mediated cellular cytoxicity (reviewed in references 7-8). The conjugates include folate linked to the Fc fragment of the IgA antibody, directly or through a linker. The Fc fragment mediates cell death by ADCC when bound to its receptor (FcαR1) on neutrophils (PMNs) (8, 9), the major white blood cells in humans. The conjugates bring activated PMNs to the proximity of FRA-expressing cancer cells and then elicit ADCC (FIG. 1).

Without being bound by theory, the conjugates will not only stimulate the PMNs to destroy the cancer cell by releasing cytotoxic molecules (10-13), but may also allow the PMNs to stimulate the production of tumor-specific antibodies (through upregulation of MHCII receptors) (14, 15), thus providing long-term protection against recurrence of the cancer. As the conjugates include FRA's natural ligand, folate, linked to the Fc portion of the IgA antibody, it is small enough to penetrate solid tumors and, upon binding its receptors, will trigger an effective ADCC response with minimal or no toxicity.

The disclosed conjugates are the first to effectively target TNBC tumors. Thus, the conjugates not only decrease mortality associated with TNBC, but do so with little or no toxicity because they directly and selectively target cancer cells. The use of the conjugates can also be applied to other cancers expressing FRA, such as ovarian and lung, both aggressive forms of cancer with high mortality rates and which folate-linked chemotherapeutic agents are currently being tested.

IgA Fc may be obtained from native forms isolated from humans and other animals including cows, goats, swine, mice, rabbits, hamsters, rats and guinea pigs, or may be recombinants or derivatives thereof, obtained from transformed animal cells or microorganisms. They may be obtained from a native immunoglobulin by isolating whole immunoglobulins from human or animal organisms and treating them with a proteolytic enzyme. Papain digests the native immunoglobulin into Fab and Fc regions, and pepsin treatment results in the production of pF'c and F(ab)2 fragments. These fragments may be subjected, for example, to size-exclusion chromatography to isolate Fc. In particular embodiments, a human-derived Fc is a recombinant Fc region that is obtained from a microorganism.

In particular embodiments, the IgA Fc portion of the conjugates can include 1) a CH1 domain, a CH2 domain, a CH3 domain and a CH4 domain, 2) a CH1 domain and a CH2 domain, 3) a CH1 domain and a CH3 domain, 4) a CH2 domain and a CH3 domain, 5) a combination of one or more domains and an immunoglobulin hinge region (or a portion of the hinge region), and/or 6) a dimer of each domain of the heavy-chain constant regions and the light-chain constant region. Also, the Fc region may contain a part or all of the Fc region including the heavy-chain constant region 1 (CH1) and/or the light-chain constant region 1 (CL1), except for the variable regions of the heavy and light chains. Also, it may be a fragment having a deletion in a relatively long portion of the amino acid sequence of CH2 and/or CH3.

The IgA Fc portion of the conjugates can include naturally-occurring IgA Fc sequences or variants thereof wherein the variants are non-naturally occurring (e.g., variant Fc regions).

Variant Fc regions can include one or more non naturally occurring amino acid residues. Also encompassed by the variant Fc regions are Fc regions which include amino acid substitutions, deletions, additions and/or modifications.

In particular embodiments, amino acid substitutions can be conservative substitutions. As used herein, a "conservative substitution" involves a substitution found in one of the following conservative substitutions groups: Group 1: Alanine (Ala or A), Glycine (Gly or G), Serine (Ser or S), Threonine (Thr or T); Group 2: Aspartic acid (Asp or D), Glutamic acid (Glu or Z); Group 3: Asparagine (Asn or N), Glutamine (Gln or Q); Group 4: Arginine (Arg or R), Lysine (Lys or K), Histidine (His or H); Group 5: Isoleucine (Ile or I), Leucine (Leu or L), Methionine (Met or M), Valine (Val or V); and Group 6: Phenylalanine (Phe or F), Tyrosine (Tyr or Y), Tryptophan (Trp or W).

Additionally, amino acids can be grouped into conservative substitution groups by similar function or chemical structure or composition (e.g., acidic, basic, aliphatic, aromatic, sulfur-containing). For example, an aliphatic grouping may include, for purposes of substitution, Gly, Ala, Val, Leu, and Ile. Other groups containing amino acids that are considered conservative substitutions for one another include: sulfur-containing: Met and Cysteine (Cys or C); acidic: Asp, Glu, Asn, and Gln; small aliphatic, nonpolar or slightly polar residues: Ala, Ser, Thr, Pro, and Gly; polar, negatively charged residues and their amides: Asp, Asn, Glu, and Gln; polar, positively charged residues: His, Arg, and Lys; large aliphatic, nonpolar residues: Met, Leu, Ile, Val, and Cys; and large aromatic residues: Phe, Tyr, and Trp. Additional information is found in Creighton (1984) Proteins, W.H. Freeman and Company.

The serum half-life of conjugates comprising Fc regions may be increased by increasing the binding affinity of the Fc region for FcRn. In one embodiment, the Fc variant protein has enhanced serum half-life relative to a comparable molecule.

Methods for generating non-naturally occurring Fc regions are known in the art. For example, amino acid substitutions and/or deletions can be generated by mutagenesis methods, including site-directed mutagenesis (Kunkel, Proc. Natl. Acad. Sci. USA 82:488-492 (1985)), PCR mutagenesis (Higuchi, in "PCR Protocols: A Guide to Methods and Applications", Academic Press, San Diego, pp. 177-183 (1990)), and cassette mutagenesis (Wells et al., Gene 34:315-323 (1985)). In particular embodiments, site-directed mutagenesis can be performed by the overlap-extension PCR method (Higuchi, in "PCR Technology: Principles and Applications for DNA Amplification", Stockton Press, New York, pp. 61-70 (1989)). The technique of overlap-extension PCR (Higuchi, ibid.) can also be used to introduce any desired mutation(s) into a target sequence (the starting DNA). For example, the first round of PCR in the overlap-extension method involves amplifying the target sequence with an outside primer (primer 1) and an internal mutagenesis primer (primer 3), and separately with a second outside primer (primer 4) and an internal primer (primer 2), yielding two PCR segments (segments A and B). The internal mutagenesis primer (primer 3) is designed to contain mismatches to the target sequence specifying the desired mutation(s). In the second round of PCR, the products of the first round of PCR (segments A and B) are amplified by PCR using the two outside primers (primers 1 and 4). The resulting full-length PCR segment (segment C) is digested with restriction enzymes and the resulting restriction fragment is cloned into an appropriate vector. As the first step of mutagenesis, the starting DNA (e.g., encoding an Fc region), is operably cloned into a mutagenesis vector. The primers are designed to reflect the desired amino acid substitution. Other methods useful for the generation of variant Fc regions are known in the art (see, e.g., U.S. Pat. Nos. 5,624,821; 5,885,573; 5,677,425; 6,165,745; 6,277,375; 5,869,046; 6,121,022; 5,624,821; 5,648,260; 6,528,624; 6,194,551; 6,737,056; 6,821,505; 6,277,375; U.S. Patent Publication Nos. 2004/0002587 and PCT Publications WO 94/29351; WO 99/58572; WO 00/42072; WO 02/060919; WO 04/029207; WO 04/099249; WO 04/063351).

Glycosylation patterns of Fc regions can also be modified to enhance ADCC. See Shields et al., JBC. 277:26733 (2002); Shinkawa et al., JBC. 278:3466 (2003) and Okazaki et al., J. Mol. Biol., 336: 1239 (2004). In some embodiments, an Fc variant includes one or more engineered glycoforms, i.e., a carbohydrate composition that is covalently attached to the molecule comprising an Fc region. Engineered glycoforms may be generated by any method known to one skilled in the art, for example by using engineered or variant expression strains, by co-expression with one or more enzymes, for example DI N-acetylglucosaminyltransferase III (GnTI11), by expressing a molecule comprising an Fc region in various organisms or cell lines from various organisms, or by modifying carbohydrate(s) after the molecule comprising Fc region has been expressed. Methods for generating engineered glycoforms are known in the art, and include those described in Umana et al., Nat. Biotechnol 17:176-180 (1999); Davies et al., Biotechnol Bioeng 74:288-294 (2001); Shields et al., J Biol Chem 277:26733-26740 (2002); Shinkawa et al., J Biol Chem 278:3466-3473 (2003); U.S. Pat. No. 6,602,684; U.S. Ser. Nos. 10/277,370; 10/113,929; PCT WO 00/61739A1; PCT WO 01/292246A1; PCT WO 02/311140A1; PCT WO 02/30954A1; Potillegent™ technology (Biowa, Inc. Princeton, N.J.); GlycoMAb™ glycosylation engineering technology (GLYCART biotechnology AG, Zurich, Switzerland); see also e.g., WO 00061739; EA01229125; US 20030115614; and Okazaki et al., JMB, 336: 1239-49 (2004). Accordingly, in particular embodiment the Fc regions of the conjugates can include altered glycosylation of amino acid residues.

As stated, the IgA Fc and folate may be linked directly or via a linker. The linker can be 1-30 amino acids in length including 1, 2, 3,4, 5, 6, 7, 8, 9, 10, 11, 12, 13, 14, 15, 16, 17, 18, 19, 20, 21, 22, 23, 24, 25, 26, 27, 28 29 or 30 amino acids in length. In one embodiment, the linker includes a single amino acid. In other embodiments, the linker includes a peptide. In some embodiments, the linker peptide can include random linker sequences that offer structural flexibilities. In some embodiments, linker peptide sequences can be selected based on the structures of individual peptide chains, by, for example, searching libraries of protein or peptide structures. In certain embodiments, a linker peptide sequence is selected to best join the structures of individual peptide chains of a dimer or multimer. In some embodiments, non-natural amino acids and/or non amino acids can be incorporated into the linker. Non-amino acid linkers include alkanes, lipids, lipid polymers, fat molecules, glycols, poly(ethylene glycol), poly (propylene glycol), copolymers of ethylene glycol and propylene glycol, polyoxyethylated polyols, polyvinyl alcohol, polysaccharides, dextran, polyvinyl ether, biodegradable polymers such as PLA (poly (lactic acid) and PLGA (poly (lactic-glycolic acid)), chitins, and hyaluronic acid. In one embodiment, the non-amino acid linker can be polyethylene glycol linked to the N-term inus of an immunoglobulin Fc region and coupled to folate.

Pharmaceutical Compositions. In some embodiments, the conjugates are provided as part of a pharmaceutical composition. The pharmaceutical composition can include, for example, at least 0.1% w/v of a conjugate. In other embodiments, the pharmaceutical composition can include between 2% to 75% of a conjugate per weight of the pharmaceutical composition, or between 25% to 60% of a conjugate per weight of the pharmaceutical composition. In particular embodiments, the conjugate content by weight can be 5%, 10%, 20%, 40%, 50%, 60%, 70%, 80%, 90% or 95% of the pharmaceutical composition.

In particular embodiments, pharmaceutical compositions can include components that complement or supplement the conjugate. For example, particular embodiments can include immune stimulants to promote a subject's immune response against cancer cells. In certain embodiments, the immune stimulant is a cytokine, an antibody, a small molecule, an siRNA, a plasmid DNA and/or a vaccine adjuvant. In additional embodiments, the components that complement or supplement the conjugate can include pain medications, nausea medications, appetite stimulants and/or fever reducers.

Any pharmaceutical composition disclosed herein can advantageously include any pharmaceutically acceptable carriers which include those that do not produce significantly adverse, allergic or other untoward reactions that outweigh the benefit of administration, whether for research, prophylactic and/or therapeutic treatments. Exemplary pharmaceutically acceptable carriers and formulations are disclosed in Remington's Pharmaceutical Sciences, 18th Ed. Mack Printing Company, 1990. Moreover, pharmaceutical compositions can be prepared to meet sterility, pyrogenicity, general safety and purity standards as required by United States FDA Office of Biological Standards and/or other relevant foreign regulatory agencies.

Exemplary generally used pharmaceutically acceptable carriers include any and all bulking agents or fillers, solvents or co-solvents, dispersion media, coatings, surfactants, antioxidants (e.g., ascorbic acid, methionine, vitamin E), preservatives, isotonic agents, absorption delaying agents, salts, stabilizers, buffering agents, chelating agents (e.g., EDTA), gels, binders, disintegration agents, and/or lubricants.

Exemplary buffering agents include citrate buffers, succinate buffers, tartrate buffers, fumarate buffers, gluconate buffers, oxalate buffers, lactate buffers, acetate buffers, phosphate buffers, histidine buffers and trimethylamine salts.

Exemplary preservatives include phenol, benzyl alcohol, meta-cresol, methyl paraben, propyl paraben, octadecyldimethylbenzyl ammonium chloride, benzalkonium halides, hexamethonium chloride, alkyl parabens such as methyl or propyl paraben, catechol, resorcinol, cyclohexanol and 3-pentanol.

Exemplary isotonic agents include polyhydric sugar alcohols including trihydric or higher sugar alcohols, such as glycerin, erythritol, arabitol, xylitol, sorbitol and mannitol.

Exemplary stabilizers include organic sugars, polyhydric sugar alcohols, polyethylene glycol; sulfur-containing reducing agents, amino acids, low molecular weight polypeptides, proteins, immunoglobulins, hydrophilic polymers and polysaccharides.

Methods of Treatment. Methods disclosed herein include treating subjects (humans, veterinary animals (dogs, cats, reptiles, birds, etc.) livestock (horses, cattle, goats, pigs, chickens, etc.) and research animals (monkeys, rats, mice, fish, etc.) with conjugates disclosed herein. Treating subjects includes delivering therapeutically effective amounts. Therapeutically effective amounts include those that provide effective amounts, prophylactic treatments and/or therapeutic treatments. Therapeutically effective amounts need not produce a full treatment or cure for a cancer but can also provide a partial treatment such as alleviation or improvement of at least one cause or symptom of the cancer.

An "effective amount" is the amount of a conjugate necessary to result in a desired physiological change in the subject. Effective amounts are often administered for research purposes. Effective amounts disclosed herein can cause a statistically-significant effect in an animal model or in vitro assay relevant to the assessment of a conjugate as an anti-cancer therapeutic.

A "prophylactic treatment" includes a treatment administered to a subject who does not display signs or symptoms of a cancer or displays only early signs or symptoms of cancer such that treatment is administered for the purpose of diminishing, preventing, or decreasing the risk of developing the cancer further. Thus, a prophylactic treatment functions as a preventative treatment against cancer.

A "therapeutic treatment" includes a treatment administered to a subject who displays symptoms or signs of cancer and is administered to the subject for the purpose of diminishing or eliminating those signs or symptoms of cancer. The therapeutic treatment can reduce, control, or eliminate the presence or activity of cancer and/or reduce control or eliminate side effects of cancer.

In the context of cancers, therapeutically effective amounts can decrease the number of cancer cells, decrease the number of metastases, decrease tumor volume, increase life expectancy, induce apoptosis of cancer cells, induce cancer cell death, inhibit angiogenesis near cancer cells, inhibit cancer cell proliferation, inhibit tumor growth, prevent metastasis, prolong a subject's life, reduce cancer-associated pain, and/or reduce relapse or re-occurrence of the cancer following treatment.

For administration, therapeutically effective amounts (also referred to herein as doses) can be initially estimated based on results from in vitro assays and/or animal model studies. Such information can be used to more accurately determine useful doses in subjects of interest.

The actual dose amount administered to a particular subject can be determined by a physician, veterinarian or researcher taking into account parameters such as physical and physiological factors including target, body weight, severity of condition, type of cancer, stage of cancer, previous or concurrent therapeutic interventions, idiopathy of the subject and route of administration.

Useful doses can range from 0.1 to 5 µg/kg or from 0.5 to 1 µg/kg. In other non-limiting examples, a dose can include 1 µg/kg, 5 µg/kg, 10 µg/kg, 15 µg/kg, 20 µg/kg, 25 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, 80 µg/kg, 85 µg/kg, 90 µg/kg, 95 µg/kg, 100 µg/kg, 150 µg/kg, 200 µg/kg, 250 µg/kg, 350 µg/kg, 400 µg/kg, 450 µg/kg, 500 µg/kg, 550 µg/kg, 600 µg/kg, 650 µg/kg, 700 µg/kg, 750 µg/kg, 800 µg/kg, 850 µg/kg, 900 µg/kg, 950 µg/kg, 1000 µg/kg, 0.1 to 5 mg/kg or from 0.5 to 1 mg/kg. In other non-limiting examples, a dose can include 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 150 mg/kg, 200 mg/kg, 250 mg/kg, 350 mg/kg, 400 mg/kg, 450 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, 1000 mg/kg or more.

Therapeutically effective amounts can be achieved by administering single or multiple doses during the course of a treatment regimen (e.g., daily, every other day, every 3 days, every 4 days, every 5 days, every 6 days, weekly, every 2 weeks, every 3 weeks, monthly, every 2 months, every 3 months, every 4 months, every 5 months, every 6 months, every 7 months, every 8 months, every 9 months, every 10 months, every 11 months or yearly).

The pharmaceutical compositions described herein can be administered by any available route including injection, inhalation, infusion, perfusion, lavage or ingestion. Routes of administration can include intravenous, intradermal, intraarterial, intraparenteral, intranasal, intranodal, intralymphatic, intraperitoneal, intralesional, intraprostatic, intravaginal, intrarectal, topical, intrathecal, intratumoral, intramuscular, intravesicular, oral, subcutaneous, and/or sublingual administration and more particularly by intravenous, intradermal, intraarterial, intraparenteral, intranasal, intranodal, intralymphatic, intraperitoneal, intralesional, intraprostatic, intravaginal, intrarectal, topical, intrathecal, intratumoral, intramuscular, intravesicular, oral, subcutaneous, and/or sublingual injection.

The Examples below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

EXAMPLES

Example 1

Figure 2:
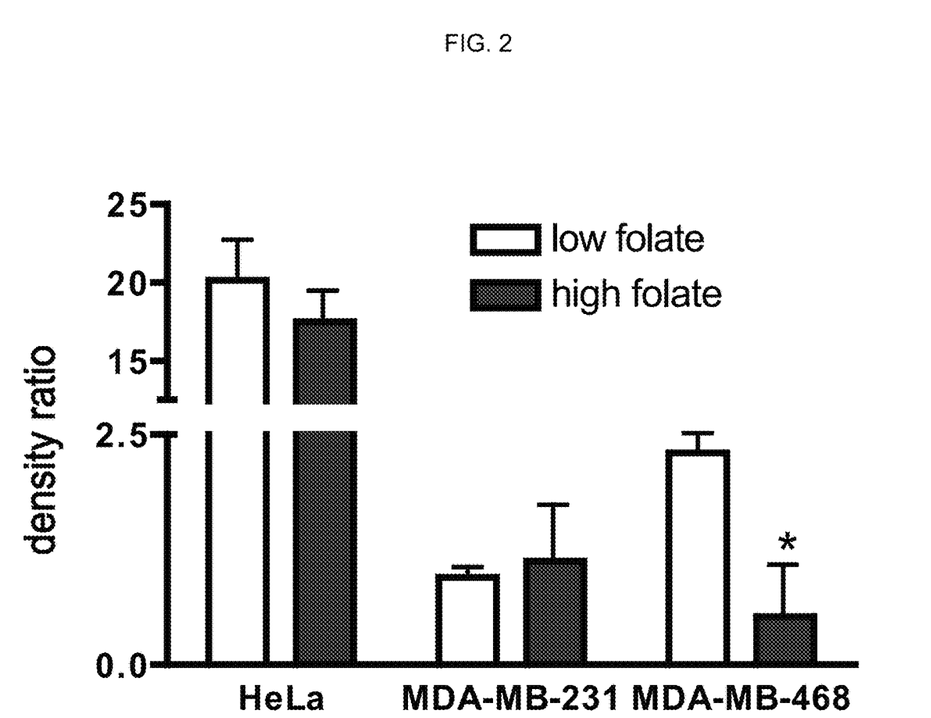
FIG. 2. FRA expression in triple negative breast cancer (TNBC) cells in the presence of high and low folate levels. Cells were grown for at least one week in either RPMI-1640 containing supra-physiological levels of folate (2.3 mM) or in folate-free RPMI and in the presence of 10% serum containing approximately 0.02 mM folate. FRA message was measured using RT-QPCR and human ovarian cancer cells (HeLa) were used as a positive control. Results are mean +/−SEM where *P<0.05 compared to low folate treated cells.
Figure 3:
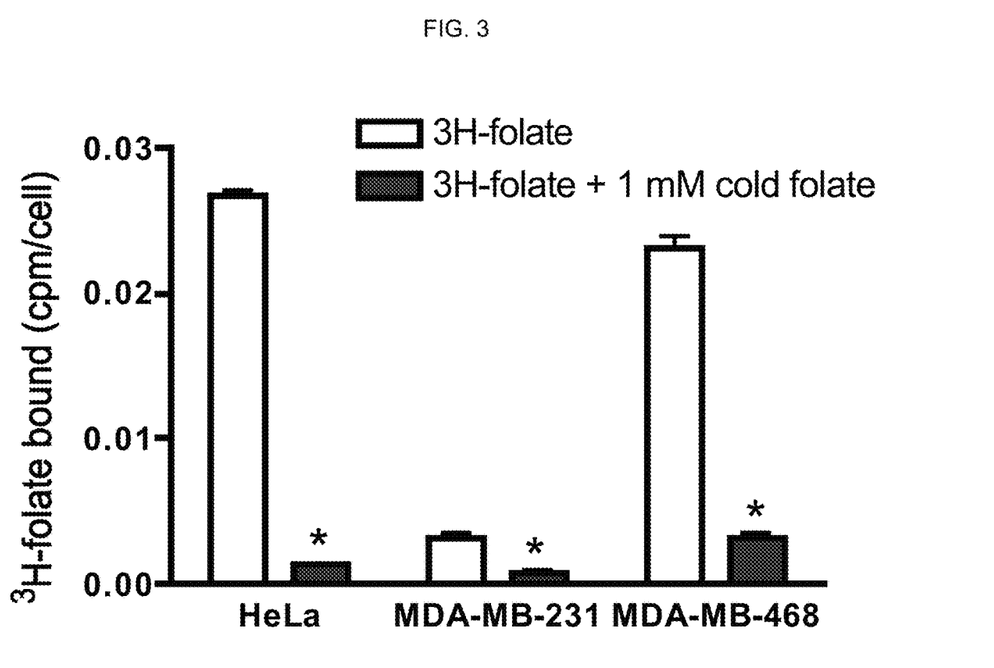
FIG. 3. Binding of folate to TNBC cells. Cells were incubated on ice for 1 hour with $^3$H-labeled folate (0.0318 mM, 14.3 Ci/mmol) in the presence or absence of cold folate (1 mM). $^3$H-folate binding was significantly inhibited in the presence of cold folate in all cell lines tested. Error shown is +/−SEM where *is P<0.05 compared to $^3$H-folate wells with no cold folate added.

Data demonstrates FRA expression on the human TNBC cell lines MDA468 and, to a lesser extent, MDA231 that are suppressed by unphysiologically high levels of folate in standard cell culture medium (FIG. 2), consistent with previous literature findings (46). With these cells growing in low-folate (physiological levels) containing media, binding assays using $^3$H-labeled folate were performed and it was found that both of these cell lines bind $^3$H-folate at levels consistent with their FRA expression profile (FIG. 3). The binding of $^3$H-folate was also inhibited in the presence of excess unlabeled folate (1 µM) confirming binding specificity.

Figure 4:
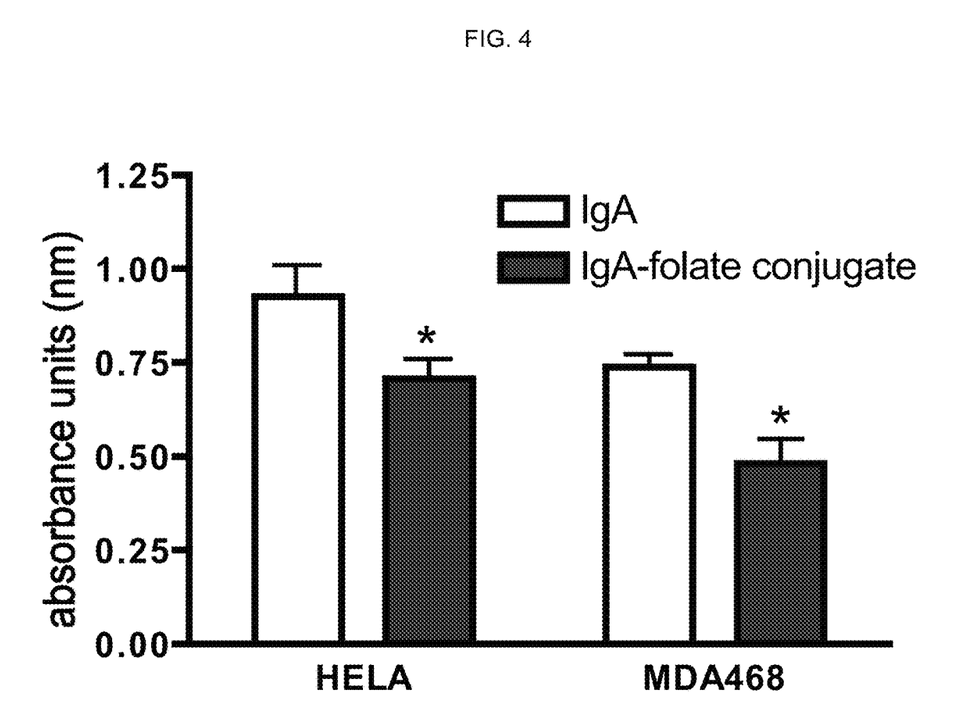

Using the FRA-expressing MDA468 cells growing in low-folate containing medium as a model system, the efficacy of conjugate NEU1 was tested by incubating these cells with freshly isolated PMNs and in the presence of NEU1, an initial conjugate including folate conjugated to whole IgA (folate-IgA), synthesized by coupling folate to amine groups on IgA using 1-ethyl-3-[3dimethylaminopropyl] carbodiimide hydrochloride (EDC; Pierce Biotechnologies). After 3-hours of incubation, there was a 30% decrease in both HeLa (positive control ovarian cancer cells) and MDA468 cell viability (MTT assay) in the presence of 5 µg/ml of folate-IgA compared to the control cells containing IgA antibody treatment alone (FIG. 4). These findings support the fact that NEU1 effectively destroys breast cancer cells. Because NEU1 had a stoichiometry of approximately one folate molecule per molecule of IgA (analyzed spectrophotometrically at 363 nM), these results are extremely encouraging given the fact that other conjugates can have a higher stoichiometry by optimizing the conjugation conditions (described below).

Example 2

Establish the effectiveness of NEU1 in vitro to kill human TNBC cells. The purpose of this Example will be to confirm the ability of NEU1 to effectively stimulate PMNs to destroy human TNBC cells through the binding and cross-linking of FcαR1 on PMNs. To do this, both MDA468 and MDA231 cells will be co-cultured with PMNs in the presence of NEU1. Signs of cancer cell stress and/or death will be assessed by performing the cellular toxicity assays described below. The experiments will be repeated utilizing PMNs from the blood, and cancer cells from the tumors, of breast cancer patients to confirm the effectiveness of NEU1, or other disclosed conjugates in the clinic.

Experimental Design & Methods.

a. Drug synthesis. For Phase I testing, conjugates will by synthesized in-house by optimizing the conditions for coupling the amine groups of the Fc-IgA fragments only to folate using EDC and N-hydroxysuccinimide (NHS; Pierce Biotechnologies). The Fc fragments will be generated using Pierce's Fab Preparation Kit followed by affinity chromatography using CaptureSelect Human IgA Affinity Matrix (Thermo Fisher) to isolate the Fc fragments. After synthesis, conjugates will be characterized by TCRS (mass spectrometry, chromatography) for drug-antibody ratio, and purity where a ratio of 3-4 folate molecules per IgA fragment will be expected. This ratio is effective in other studies utilizing folate conjugated to whole antibodies (47).

b. Recruitment of patients for blood and tumor tissue collection. Blood will be collected from healthy volunteers using an approved IRB protocol. Breast cancer patients will be identified and recruited. The surgeons will identify and obtain consent from patients during their clinic visit with the surgeon. On the day of surgery, routine phlebotomy will be performed by the attending nurse, just prior to surgery, to obtain 50 ml of peripheral blood. This volume will be sufficient to obtain the amount of PMNs required for the experimental procedures. PMN will be isolated from the blood by Ficoll/dextran density gradient centrifugation (48). Tumor tissue will be obtained from the pathologist. Once the specimen is received in the tissue laboratory (within 30 min of removal from patient), a portion of tumor (1.0 cm$^3$) will be retrieved, a 2-3 mm section from this will be fixed in formalin and a Hematoxylin and Eosin section obtained and reviewed by the pathologist to ascertain appropriateness of the tissue for the research. Based on previous experience, this size tissue will yield 2-4 million cancer cells, enough to perform the experiments outlined in both Examples. Cells for Example 3 will be stored in liquid nitrogen until needed. The tissue/blood will be handled appropriately to maintain viability and samples will be used immediately.

c. FRA expression analysis. Tumor tissue will be digested using Miltenyi Biotec's Tumor Dissociation kit and the cancer cells isolated by growth in selective medium as previously described (49). After isolation, FRA gene expression will be confirmed within one hour by FACs analysis (MICR core) using HeLa cells as a positive control and, if present, the co-culture experiments described below will be conducted. If FRA is not expressed on the breast cancer isolates, then the cells will be subcultured in the presence of dexamethasone for 2 days to induce FRA expression (50) prior to performing the co-culture experiments.

d. Co-culture assays. MDA468 or MDA231 cells will be co-cultured with the PMNs at a ratio of 1:10, respectively, and in the presence or absence of 1 or 10 µg/ml of conjugate for 3 hours or overnight. Because most cell culture medium contains supra-physiological levels of folate, the cells will be grown in RPMI medium lacking folate but normal amounts of serum that contains physiological amounts of folate (5-50 nM). These doses, cell ratios and time points were used in generating the data described in Example 1 or were chosen based on previous folate-antibody or PMN FcαR1-stimulation experiments (10, 11, 14, 47, 51). At the end of these time points, ADCC of the cancer cells will be assessed by the traditional Cr$^{51}$ release assay. In addition, immuno-microscopic analysis will be performed on cytospin preparations looking for characteristic apoptotic/autophagic markers (Annexin V, p62). Human IgA will be used as a negative control and an excess amount of folate (1 mM) will be used to confirm the role of FRA in mediating the cellular cytotoxic effects induced by conjugate. The purity of PMNs will be determined by FACS analysis (CD15+, CD11b+) and only those demonstrating 95% or greater purity will be used.

Using blood PMNs and FRA-expressing breast cancer cells isolated from tumors, the experiments will be performed as patients become available. If FRA expression has to be induced, PMNs from healthy controls will be used in the co-cultures. The experiments will likely be performed on 10 TNBC isolates.

Data Analysis & Interpretation. The co-culture experiments will be performed 3 times with the cell lines and once for each clinical sample with individual assays plated in triplicate. The objective of this study is to test for cancer cell death. Medians and interquartile ranges will be estimated and the data displayed graphically using boxplots (WSU Biostatistical core). Statistically significant results will be obtained showing that the conjugate will effectively induce ADCC to destroy breast cancer cells. If statistically significant results are not obtained, the conjugate will be optimized further by, for example, inclusion of a linker or a change in stoichiometry. Effectiveness may also be increased using cytokines that have been shown to increase FcαR1 expression or activity (53, 55). In addition, the dosing of a conjugate may need to be optimized for maximum efficacy. Using one or more of these approaches, statistically significant results will be obtained showing that the optimized conjugate will effectively induce ADCC to destroy breast cancer cells.

Example 3

Assess the effectiveness of conjugate in breast tumor models. Because mice do not express FcαR1 due to a translocation of this gene (56), BALB/c mice in which the human FcαR1 gene has been inserted will be used to test the efficacy of conjugate (e.g., NEU1) in vivo to kill mouse 4T1 cancer cells which express high levels of FRA and have been used successfully to target folate-conjugated drugs into these cells (57-59). This is a syngeneic model that will allow ascertainment of the effectiveness of conjugate in the presence of a fully functional immune system. To test the in vivo efficacy of conjugate on human cancer cells, BALB/c scid mice will be used where the human FcαR1 gene will be introduced by backcrossing with FcαR1-expressing BALB/c mice. Because BALB/c scid mice carry the severe combined immune deficiency mutation (scid), they lack functional T and B cells but have a normal population of PMN, NK and macrophages that will allow testing of the in vivo efficacy of conjugate on both the MDA231 cell line and on the cancer cells isolated from the tumors of the TNBC patients (clinical isolates).

Experimental Design & Methods. Backcrossing services will be performed by the animal services core facility at Wayne State University to backcross the BALB/c mice expressing human FcαR1 (BALB/c+) into BALB/c scid mice. Mice will be put on a low-folate containing diet (TD.95247; Harlan) for one week prior to performing any studies. The concentration of folate in this diet is 0.1-0.2 mg/kg bw compared to normal rodent chow which contains supra-physiological levels of folate (2.5-3.0 mg/kg). Toxicity studies will be performed on BALB/c mice to determine the maximum tolerated dose (MTD) of conjugate (5 to 100 mg/kg bw) by observing the mice for signs of intolerance in accordance with our institute's IACUC department. These doses were chosen based on doses established previously for testing monoclonal FRA antibodies in mice (38, 60). Once the MTD of conjugate has been determined, 5week-old BALB/c+ and BALB/c− (negative control) mice will be injected with 1×10$^5$ FRA-expressing 4T1 cells in accordance with an IACUC approved protocol. Once tumors are palpable, mice will be divided into groups of 6 and treated with either conjugate or vehicle (PBS) at the MTD intravenously (IV) three times weekly for 5-8 weeks or until tumors reach 1000 mm$^3$ (61). Tumor size will be measured two to three times a week using a Vernier caliper and tumor volume calculated using the following formula: length×width×depth/2. This study will be repeated in 5 week-old BALB/c+ scid and BALB/c− scid (negative control) mice using 5×10$^5$ MDA231 cells or clinical isolates.

Data Analysis & Interpretation. At the end of each study, tumors will be removed and formalin, paraffin-embedded. Sections will be deparaffinized and immunostained for signs of cell death (Annexin V, p62), cell viability (Ki-67) and presence of PMNS (Ly6G+,CD11b+). Tumor volume will be graphed and a statistically significant decrease in tumor volume will be observed and used as a criteria for success.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. As used herein, a material effect would cause a statistically-significant reduction in the ability of a conjugate to treat breast cancer in a subject.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, $3^{rd}$ Edition or a dictionary known to those of ordinary skill in the art, such as the Oxford Dictionary of Biochemistry and Molecular Biology (Ed. Anthony Smith, Oxford University Press, Oxford, 2004).

REFERENCES

1. Siegel R aJA: Cancer Statistics 2014, Cancer Journal for Clinicians 2014, Published online ahead of print at cacancerjournal.com. doi: 10.3322/caac.21208.:
2. Cleere D W: Triple-negative breast cancer: a clinical update, Community Oncology 2010, 7:203-211
3. BreastCancer.org: How triple-negative breast cancer behaves and looks., 2013,
4. O'Shannessy D J, Somers E B, Albone E, Cheng X, Park Y C, Tomkowicz B E, Hamuro Y, Kohl T O, Forsyth T M, Smale R, Fu Y S, Nicolaides N C: Characterization of the human folate receptor alpha via novel antibody-based probes, Oncotarget 2011, 2:1227-1243
5. Weitman S D, Weinberg A G, Coney L R, Zurawski V R, Jennings D S, Kamen B A: Cellular localization of the folate receptor: potential role in drug toxicity and folate homeostasis, Cancer research 1992, 52:6708-6711
6. O+Shannessy D J, Somers E B, Maltzman J, Smale R, Fu Y S: Folate receptor alpha (FRA) expression in breast cancer: identification of a new molecular subtype and association with triple negative disease, SpringerPlus 2012, 1:22
7. Zhang Z, Wang J, Tacha D E, Li P, Bremer R E, Chen H, Wei B, Xiao X, Da J, Skinner K, Hicks D G, Bu H, Tang P: Folate Receptor alpha Associated With Triple-Negative Breast Cancer and Poor Prognosis, Archives of pathology & laboratory medicine 2013,
8. Otten M A, van Egmond M: The Fc receptor for IgA (FcalphaRI, CD89), Immunol Lett 2004, 92:23-31
9. van Egmond M, Damen C A, van Spriel A B, Vidarsson G, van Garderen E, van de Winkel J G: IgA and the IgA Fc receptor, Trends in immunology 2001, 22:205-211
10. Bakema J E, Ganzevles S H, Fluitsma D M, Schilham M W, Beelen R H, Valerius T, Lohse S, Glennie M J, Medema J P, van Egmond M: Targeting FcalphaRI on polymorphonuclear cells induces tumor cell killing through autophagy, J Immunol 2011, 187:726-732
11. Otten M A, Rudolph E, Dechant M, Tuk C W, Reijmers R M, Beelen R H, van de Winkel J G, van Egmond M: Immature neutrophils mediate tumor cell killing via IgA but not IgG Fc receptors, J Immunol 2005, 174:5472-5480
12. Valerius T, Elsasser D, Repp R, Van de Winkel J G, Gramatzki M, Glennie M: HLA class II antibodies recruit G-CSF activated neutrophils for treatment of B cell malignancies, Leukemia & lymphoma 1997, 26:261-269
13. van Egmond M: Neutrophils in antibody-based immunotherapy of cancer, Expert opinion on biological therapy 2008, 8:83-94
14. Abi Abdallah D S, Egan C E, Butcher B A, Denkers E Y: Mouse neutrophils are professional antigen-presenting cells programmed to instruct Th1 and Th17 T-cell differentiation, Int Immunol 2011, 23:317-326
15. Fridlender Z G, Sun J, Mishalian I, Singhal S, Cheng G, Kapoor V, Horng W, Fridlender G, Bayuh R, Worthen G S, Albelda S M: Transcriptomic analysis comparing tumor-associated neutrophils with granulocytic myeloid-derived suppressor cells and normal neutrophils, PLoS One 2012, 7:e31524
16. Comfort C: The breast cancer drug market will remain largely static over the next decade, owing to the generic erosion of key agents and a substantial reduction in the prescribing of Roche/Genentech/Chugai's Avastin. Decision Resources. http://decisionresources.com/News-and-Events/Press-Releases/breast-cancer-040711-sthash.qbUy3rsq.dpuf, April 2011,
17. Duval A, Buckley, N., Isherwood, A.: Breast Cancer (Event Driven), http://bio-trendscom/Products-and-Services/Report?r=pcoron0214 Aug. 15, 2013,
18. DecisionBase: Breast Cancer (Triple-Negative, Advanced/Metastatic), DecisionBase; http://decisionresourcescom/Products-and-Services/Report?r=dbason0214 April 2014,
19. EORTC: EORTC, BIG and TESARO launch registration trial with niraparib for patients with metastatic BRCA mutated breast cancer, EORTCorg; http://wwweortcorg/news/eortc-big-and-tesaro-launch-registration-trial-niraparib-patients-metastatic-brca-mutated-breas November 2013,
20. Pohlmann P R, Mayer I A, Mernaugh R: Resistance to Trastuzumab in Breast Cancer, Clinical cancer research : an official journal of the American Association for Cancer Research 2009, 15:7479-7491
21. Clynes R A, Towers T L, Presta L G, Ravetch J V: Inhibitory Fc receptors modulate in vivo cytotoxicity against tumor targets, Nature medicine 2000, 6:443-446
22. Garcia-Foncillas J, Diaz-Rubio E: Progress in metastatic colorectal cancer: growing role of cetuximab to optimize clinical outcome, Clinical & translational oncology: official publication of the Federation of Spanish Oncology Societies and of the National Cancer Institute of Mexico 2010, 12:533-542
23. Pullarkat V, Deo Y, Link J, Spears L, Marty V, Curnow R, Groshen S, Gee C, Weber J S: A phase I study of a HER2/neu bispecific antibody with granulocyte-colony-stimulating factor in patients with metastatic breast cancer that overexpresses HER2/neu, Cancer Immunol Immunother 1999, 48:9-21
24. Repp R, van Ojik H H, Valerius T, Groenewegen G, Wieland G, Oetzel C, Stockmeyer B, Becker W, Eisenhut M, Steininger H, Deo Y M, Blijham G H, Kalden J R, van de Winkel J G, Gramatzki M: Phase I clinical trial of the bispecific antibody MDX-H210 (anti-FcgammaRIx anti-HER-2/neu) in combination with Filgrastim (G-CSF) for treatment of advanced breast cancer, British journal of cancer 2003, 89:2234-2243
25. Curnow R T: Clinical experience with CD64-directed immunotherapy. An overview, Cancer Immunol Immunother 1997, 45:210-215
26. Ravetch J V, Bolland S: IgG Fc receptors, Annu Rev Immunol 2001, 19:275-290
27. Hamre R, Farstad I N, Brandtzaeg P, Morton H C: Expression and modulation of the human immunoglobulin A Fc receptor (CD89) and the FcR gamma chain on myeloid cells in blood and tissue, Scandinavian journal of immunology 2003, 57:506-516
28. Deo Y M, Sundarapandiyan K, Keler T, Wallace P K, Graziano R F: Bispecific molecules directed to the Fc receptor for IgA (Fc alpha RI, CD89) and tumor antigens efficiently promote cell-mediated cytotoxicity of tumor targets in whole blood, J Immunol 1998, 160:1677-1686
29. Guettinger Y, Barbin K, Peipp M, Bruenke J, Dechant M, Horner H, Thierschmidt D, Valerius T, Repp R, Fey GH, Stockmeyer B: A recombinant bispecific single-chain fragment variable specific for HLA class II and Fc alpha RI (CD89) recruits polymorphonuclear neutrophils for efficient lysis of malignant B lymphoid cells, J Immunol 2010, 184:1210-1217
30. Huls G, Heijnen I A, Cuomo E, van der Linden J, Boel E, van de Winkel J G, Logtenberg T: Antitumor immune effector mechanisms recruited by phage display-derived fully human IgG1 and IgA1 monoclonal antibodies, Cancer research 1999, 59:5778-5784
31. Lohse S, Derer S, Beyer T, Klausz K, Peipp M, Leusen J H, van de Winkel J G, Dechant M, Valerius T: Recombinant dimeric IgA antibodies against the epidermal growth factor receptor mediate effective tumor cell killing, J Immunol 2011, 186:3770-3778
32. Stockmeyer B, Elsasser D, Dechant M, Repp R, Gramatzki M, Glennie M J, van de Winkel J G, Valerius T: Mechanisms of G-CSF- or GM-CSF-stimulated tumor cell killing by Fc receptor-directed bispecific antibodies, Journal of immunological methods 2001, 248:103-111
33. van Egmond M, van Spriel A B, Vermeulen H, Huls G, van Garderen E, van de Winkel J G: Enhancement of polymorphonuclear cell-mediated tumor cell killing on simultaneous engagement of fcgammaRI (CD64) and fcalphaRI (CD89), Cancer research 2001, 61:4055-4060
34. Bakema J E, van Egmond M: Immunoglobulin A: A next generation of therapeutic antibodies?, mAbs 2011, 3:352-361
35. Stewart W W, Mazengera R L, Shen L, Kerr M A: Unaggregated serum IgA binds to neutrophil Fc alpha R at physiological concentrations and is endocytosed but cross-linking is necessary to elicit a respiratory burst, Journal of leukocyte biology 1994, 56:481-487
36. Low P S, Kularatne S A: Folate-targeted therapeutic and imaging agents for cancer, Current opinion in chemical biology 2009, 13:256-262
37. Feuerstein A: Endocyte Falls on Ovarian Cancer Drug Blowup, The Street May 2014,
38. Ebel W, Routhier E L, Foley B, Jacob S, McDonough J M, Patel R K, Turchin H A, Chao Q, Kline J B, Old L J, Phillips M D, Nicolaides N C, Sass P M, Grasso L: Preclinical evaluation of MORAb-003, a humanized monoclonal antibody antagonizing folate receptor-alpha, Cancer immunity 2007, 7:6
39. Dillman R O: Perceptions of Herceptin: a monoclonal antibody for the treatment of breast cancer, Cancer biotherapy & radiopharmaceuticals 1999, 14:5-10
40. Green M C, Murray J L, Hortobagyi G N: Monoclonal antibody therapy for solid tumors, Cancer treatment reviews 2000, 26:269-286
41. Rudnick S I, Lou J, Shaller C C, Tang Y, Klein-Szanto A J, Weiner L M, Marks J D, Adams G P: Influence of affinity and antigen internalization on the uptake and penetration of Anti-HER2 antibodies in solid tumors, Cancer research 2011, 71:2250-2259
42. Stover P J: Physiology of folate and vitamin B12 in health and disease, Nutrition reviews 2004, 62:S3-12; discussion S13
43. Elnakat H, Ratnam M: Distribution, functionality and gene regulation of folate receptor isoforms: implications in targeted therapy, Advanced drug delivery reviews 2004, 56:1067-1084
44. Parker N, Turk M J, Westrick E, Lewis J D, Low P S, Leamon C P: Folate receptor expression in carcinomas and normal tissues determined by a quantitative radioligand binding assay, Analytical biochemistry 2005, 338:284-293
45. Weitman S D, Lark R H, Coney L R, Fort D W, Frasca V, Zurawski V R, Jr., Kamen B A: Distribution of the folate receptor GP38 in normal and malignant cell lines and tissues, Cancer research 1992, 52:3396-3401
46. Kane M A, Elwood P C, Portillo R M, Antony A C, Najfeld V, Finley A, Waxman S, Kolhouse J F: Influence on immunoreactive folate-binding proteins of extracellular folate concentration in cultured human cells, The Journal of clinical investigation 1988, 81:1398-1406
47. Cho B K, Roy E J, Patrick T A, Kranz D M: Single-chain Fv/folate conjugates mediate efficient lysis of folate-receptor-positive tumor cells, Bioconjugate chemistry 1997, 8:338-346
48. Speyer C L, Gao H, Rancilio N J, Neff T A, Huffnagle G B, Sarma J V, Ward P A: Novel chemokine responsiveness and mobilization of neutrophils during sepsis, The American journal of pathology 2004, 165:2187-2196
49. Ethier S P, Mahacek M L, Gullick W J, Frank T S, Weber B L: Differential isolation of normal luminal mammary epithelial cells and breast cancer cells from primary and metastatic sites using selective media, Cancer research 1993, 53:627-635
50. Tran T, Shatnawi A, Zheng X, Kelley K M, Ratnam M: Enhancement of folate receptor alpha expression in tumor cells through the glucocorticoid receptor: a promising means to improved tumor detection and targeting, Cancer research 2005, 65:4431-4441
51. Iking-Konert C, Vogt S, Radsak M, Wagner C, Hansch G M, Andrassy K: Polymorphonuclear neutrophils in Wegener's granulomatosis acquire characteristics of antigen presenting cells, Kidney Int 2001, 60:2247-2262
52. van Egmond M, van Vuuren A J, Morton H C, van Spriel A B, Shen L, Hofhuis F M, Saito T, Mayadas T N, Verbeek J S, van de Winkel J G: Human immunoglobulin A receptor (FcalphaRI, CD89) function in transgenic mice requires both FcR gamma chain and CR3 (CD11b/CD18), Blood 1999, 93:4387-4394
53. Weisbart R H, Kacena A, Schuh A, Golde D W: GM-CSF induces human neutrophil IgA-mediated phagocytosis by an IgA Fc receptor activation mechanism, Nature 1988, 332:647-648
54. Morton H C, van Egmond M, van de Winkel J G: Structure and function of human IgA Fc receptors (Fc alpha R), Critical reviews in immunology 1996, 16:423-440
55. Monteiro R C, Van De Winkel J G: IgA Fc receptors, Annu Rev Immunol 2003, 21:177-204
56. Reljic R: In search of the elusive mouse macrophage Fc-alpha receptor, Immunol Lett 2006, 107:80-81
57. Prabaharan M, Grailer J J, Pilla S, Steeber D A, Gong S: Gold nanoparticles with a monolayer of doxorubicin-conjugated amphiphilic block copolymer for tumor-targeted drug delivery, Biomaterials 2009, 30:6065-6075
58. Prabaharan M, Grailer J J, Pilla S, Steeber D A, Gong S: Folate-conjugated amphiphilic hyperbranched block copolymers based on Boltorn H40, poly(L-lactide) and poly(ethylene glycol) for tumor-targeted drug delivery, Biomaterials 2009, 30:3009-3019
59. Prabaharan M, Grailer J J, Steeber D A, Gong S: Thermosensitive micelles based on folate-conjugated poly(N-vinylcaprolactam)-block-poly(ethylene glycol) for tumor-targeted drug delivery, Macromolecular bioscience 2009, 9:744-753
60. Li H, Lu Y, Piao L, Wu J, Yang X, Kondadasula S V, Carson W E, Lee R J: Folate-immunoglobulin G as an anticancer therapeutic antibody, Bioconjugate chemistry 2010, 21:961-968
61. Speyer C L, Smith J S, Banda M, DeVries J A, Mekani T, Gorski D H: Metabotropic glutamate receptor-1: a potential therapeutic target for the treatment of breast cancer, Breast cancer research and treatment 2012, 132:565-573

What is claimed is:

1. A method of treating folate-receptor alpha (FRA)-expressing cancer in a subject in need thereof comprising administering a therapeutically effective amount of a conjugate comprising (i) an Fc portion of an IgA antibody, wherein said Fc portion comprises a CH2 domain and a CH3 domain but does not comprise a hinge region, and (ii) folate to the subject thereby treating FRA-expressing cancer in the subject.

2. A method of claim 1 wherein the conjugate further comprises a linker.

3. A method of claim 2 wherein the linker is a peptide linker.

4. A method of claim 2 wherein the linker is a non-peptide linker.

5. A method of claim 1 wherein the Fc portion is a variant Fc.

6. A method of claim 1 wherein the folate is a folate analog.

7. A method of claim 1 wherein the Fc portion is a variant Fc and the folate is a folate analog.

8. A method of claim 1 wherein the cancer is breast cancer, ovarian cancer or lung cancer.

9. A method of claim 1 wherein the cancer is triple negative breast cancer.

10. A method of claim 1 wherein the cancer includes cancer cells that lack receptors for one or more of estrogen, progesterone and epithelial growth factor.

11. A pharmaceutical composition comprising a conjugate comprising (i) an Fc portion of an IgA antibody, wherein said Fc portion comprises a CH2 domain and a CH3 domain but does not comprise a hinge region, and (ii) folate.

12. A pharmaceutical composition of claim 11 wherein the conjugate further comprises a linker.

13. A pharmaceutical composition of claim 12 wherein the linker is a peptide linker.

14. A pharmaceutical composition of claim 12 wherein the linker is a non-peptide linker.

15. A pharmaceutical composition of claim 11 wherein the Fc portion is a variant Fc.

16. A pharmaceutical composition of claim 11 wherein the folate is a folate analog.

17. A pharmaceutical composition of claim 11 wherein the Fc portion is a variant Fc and the folate is a folate analog.

18. The method of claim 1, wherein the $Fc_2$ fragment consists of a CH2/CH3 region from an IgA antibody.

19. The pharmaceutical composition of claim 11, wherein the $Fc_2$ fragment consists of a CH2/CH3 region from an IgA antibody.

* * * * *